US006171326B1

(12) United States Patent
Ferrera et al.

(10) Patent No.: US 6,171,326 B1
(45) Date of Patent: Jan. 9, 2001

(54) THREE DIMENSIONAL, LOW FRICTION VASOOCCLUSIVE COIL, AND METHOD OF MANUFACTURE

(75) Inventors: David A. Ferrera, San Francisco; Daniel R. Kurz, Sunnyvale; Peter Wilson, Foster City; Crystal K. Sein-Lwyn, Hayward; Lok A. Lei, San Jose, all of CA (US)

(73) Assignee: Micrus Corporation, Mountain View, CA (US)

( * ) Notice: Under 35 U.S.C. 154(b), the term of this patent shall be extended for 0 days.

(21) Appl. No.: 09/140,495

(22) Filed: Aug. 27, 1998

(51) Int. Cl.[7] .................................................. A61M 29/00
(52) U.S. Cl. ............................................................. 606/191
(58) Field of Search .................................. 606/191, 200, 606/70, 194, 106; 604/104

(56) References Cited

U.S. PATENT DOCUMENTS

| 1,341,052 | 5/1920 | Gale . |
| 1,667,730 | 5/1928 | Green . |

(List continued on next page.)

FOREIGN PATENT DOCUMENTS

| 4102550 A1 | 8/1991 | (DE) . |
| 0 183372 A1 | 6/1986 | (EP) . |

(List continued on next page.)

OTHER PUBLICATIONS

"Shape Memory Alloys" by Jeff Perkins, pp. 1095–1096.
International Search Report dated Dec. 9, 1999.
Christos A. Athanasoulis, M.D. The New England Journal of Medicine, May 15, 1980 "Therapeutic Applications of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

Alex Berenstein, M.D. and Irvin I. Kricheff, M.D. "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

(List continued on next page.)

*Primary Examiner*—Michael Buiz
*Assistant Examiner*—(Jackie) Tan-Uyen T. Ho
(74) *Attorney, Agent, or Firm*—Fulwider Patton Lee & Utecht, LLP

(57) ABSTRACT

The three dimensional, low friction vasoocclusive coil has a distal portion that is three dimensionally shaped, and a proximal portion that is linear or helically shaped. The distal three dimensional portion will form a basket for filling the anatomical cavity at the site in the vasculature to be treated, while the proximal portion will fill and reinforce the basket. The vasoocclusive device is formed from at least one strand of a flexible material formed to have an first inoperable, substantially linear configuration for insertion into and through a catheter or cannula to a desired portion of the vasculature to be treated, and a second operable, three dimensional configuration for occluding the desired portion of the vasculature to be treated. The vasoocclusive device has a distal portion having a second operable, three dimensional shape for filing the anatomical cavity at the site in the vasculature to be treated, and a proximal portion having a second operable, substantially linear shape for filling and reinforcing the distal, three dimensional shaped portion when it is implanted at the site in the vasculature to be treated. Mandrels are provided for use in the method of making the vasoocclusive device.

49 Claims, 9 Drawing Sheets

U.S. PATENT DOCUMENTS

| | | |
|---|---|---|
| 2,078,182 | 4/1937 | MacFarland . |
| 2,549,335 | 4/1951 | Rahthus . |
| 3,334,629 | 8/1967 | Cohn . |
| 3,649,224 | 3/1972 | Anderson et al. . |
| 3,868,956 | 3/1975 | Alfidi et al. . |
| 4,494,531 | 1/1985 | Gianturco . |
| 4,512,338 * | 4/1985 | Balko et al. ......................... 606/191 |
| 4,531,933 | 7/1985 | Norton et al. . |
| 4,638,803 | 1/1987 | Rand . |
| 4,655,771 | 4/1987 | Wallsten . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,832,055 | 5/1989 | Palestrant . |
| 4,850,960 | 7/1989 | Grayzel . |
| 4,856,516 | 8/1989 | Hillstead . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | Wilkoff . |
| 4,994,069 * | 2/1991 | Ritchart et al. ...................... 606/191 |
| 5,026,377 | 6/1991 | Burton et al. . |
| 5,041,084 | 8/1991 | DeVries et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,122,136 | 6/1992 | Guglielmi et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,456 | 8/1993 | Silvestrini . |
| 5,250,071 | 10/1993 | Palermo . |
| 5,261,916 | 11/1993 | Engelson . |
| 5,304,194 | 4/1994 | Chee et al. . |
| 5,304,195 | 4/1994 | Twyford, Jr. et al. . |
| 5,312,415 | 5/1994 | Palermo . |
| 5,314,472 | 5/1994 | Fontaine . |
| 5,334,210 | 8/1994 | Gianturco . |
| 5,336,205 | 8/1994 | Zenzen et al. . |
| 5,342,387 | 8/1994 | Summers . |
| 5,350,397 | 9/1994 | Palermo et al. . |
| 5,354,295 | 10/1994 | Guglielmi et al. . |
| 5,370,683 | 12/1994 | Fontaine . |
| 5,382,259 | 1/1995 | Phelps et al. . |
| 5,423,829 | 6/1995 | Pham et al. . |
| 5,441,516 | 8/1995 | Wang et al. . |
| 5,443,478 | 8/1995 | Purdy . |
| 5,514,176 | 5/1996 | Bosley, Jr. . |
| 5,522,822 | 6/1996 | Phelps et al. . |
| 5,522,836 | 6/1996 | Palermo . |
| 5,527,354 | 6/1996 | Fontaine et al. . |
| 5,536,274 | 7/1996 | Neuss . |
| 5,549,624 | 8/1996 | Mirigian et al. . |
| 5,562,641 | 10/1996 | Flomenblit et al. . |
| 5,562,698 | 10/1996 | Parker . |
| 5,569,245 | 10/1996 | Guglielmi et al. . |
| 5,582,619 | 12/1996 | Ken . |
| 5,607,445 | 3/1997 | Summers . |
| 5,624,449 | 4/1997 | Pham et al. . |
| 5,624,461 | 4/1997 | Mariant . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,082 | 7/1997 | Sung et al. . |
| 5,645,558 | 7/1997 | Horton . |
| 5,649,949 | 7/1997 | Wallace et al. . |
| 5,667,522 | 9/1997 | Flomenblit et al. . |
| 5,669,931 | 9/1997 | Kupiecki et al. . |
| 5,676,697 | 10/1997 | McDonald . |
| 5,685,322 | 11/1997 | Sung et al. . |
| 5,690,643 | 11/1997 | Wijay . |
| 5,690,666 | 11/1997 | Berenstein et al. . |
| 5,690,671 | 11/1997 | McGurk et al. . |
| 5,700,258 | 12/1997 | Mirigian et al. . |
| 5,707,389 * | 1/1998 | Louw et al. ......................... 606/170 |
| 5,718,711 | 2/1998 | Berenstein et al. . |
| 5,725,546 | 3/1998 | Samson . |
| 5,725,552 | 3/1998 | Kotula et al. . |
| 5,733,329 | 3/1998 | Wallace et al. . |
| 5,749,891 | 5/1998 | Ken et al. . |
| 5,749,894 * | 5/1998 | Engelson et al. ................... 606/191 |
| 5,766,160 | 6/1998 | Samson et al. . |
| 5,843,118 * | 12/1998 | Sepetka et al. ...................... 606/194 |

FOREIGN PATENT DOCUMENTS

| | | |
|---|---|---|
| 0 382014 A1 | 8/1990 | (EP) . |
| 0 747 013 A1 | 12/1996 | (EP) . |
| 0 747 014 A1 | 12/1996 | (EP) . |
| 0 743 047 A3 | 3/1997 | (EP) . |
| 0 765 636 A2 | 4/1997 | (EP) . |
| 0 820 726 A2 | 1/1998 | (EP) . |
| 592.182 | 7/1925 | (FR) . |
| 2 066 839 | 7/1981 | (GB) . |
| WO 92/14408 | 9/1992 | (WO) . |
| WO 94/09705 | 5/1994 | (WO) . |
| WO 97/31672 | 9/1997 | (WO) . |
| WO 97/48351 | 12/1997 | (WO) . |
| WO 98/09570 | 3/1998 | (WO) . |
| WO 99/29260 | 6/1999 | (WO) . |

OTHER PUBLICATIONS

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978 "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace, M.D. et al., Cancer, Oct. 1979 "Arterial Occlusion of Pelvic Bone Tumors"; pp. 322–325 & 661–663.

"Mechanical Devices for Arterial Occlusion" By C. Gianturco, M.D., et al., Jul. 1975 pp. 428–435.

"Therapeutic Vascular Occlusion Utilizing Steel Coil Technique: Clinical Applications" By Sidney Wallace, et al., Am J. Roentgenol (1976); pp. 381–387.

"Transcatheter Intravascular Coil Occlusion of Experimental Arteriovenous Fistulas", By James H. Anderson, et al., Am. J. Roentgenol, Nov. 1977, pp.795–798.

" 'Mini' Gianturco Stainless Steel Coils for Transcatheter Vascular Occlusion" By James H. Anderson, et al., From the Department of Diagnostic Radiology at the University of Texas System Cancer Center , Aug. 1978, pp. 301–303.

"A New Improved Coil for Tapered–Tip Catheter for Arterial Occlusion" By Vincent P. Chuang, M.D., et al., May 1980, pp. 507–509.

* cited by examiner

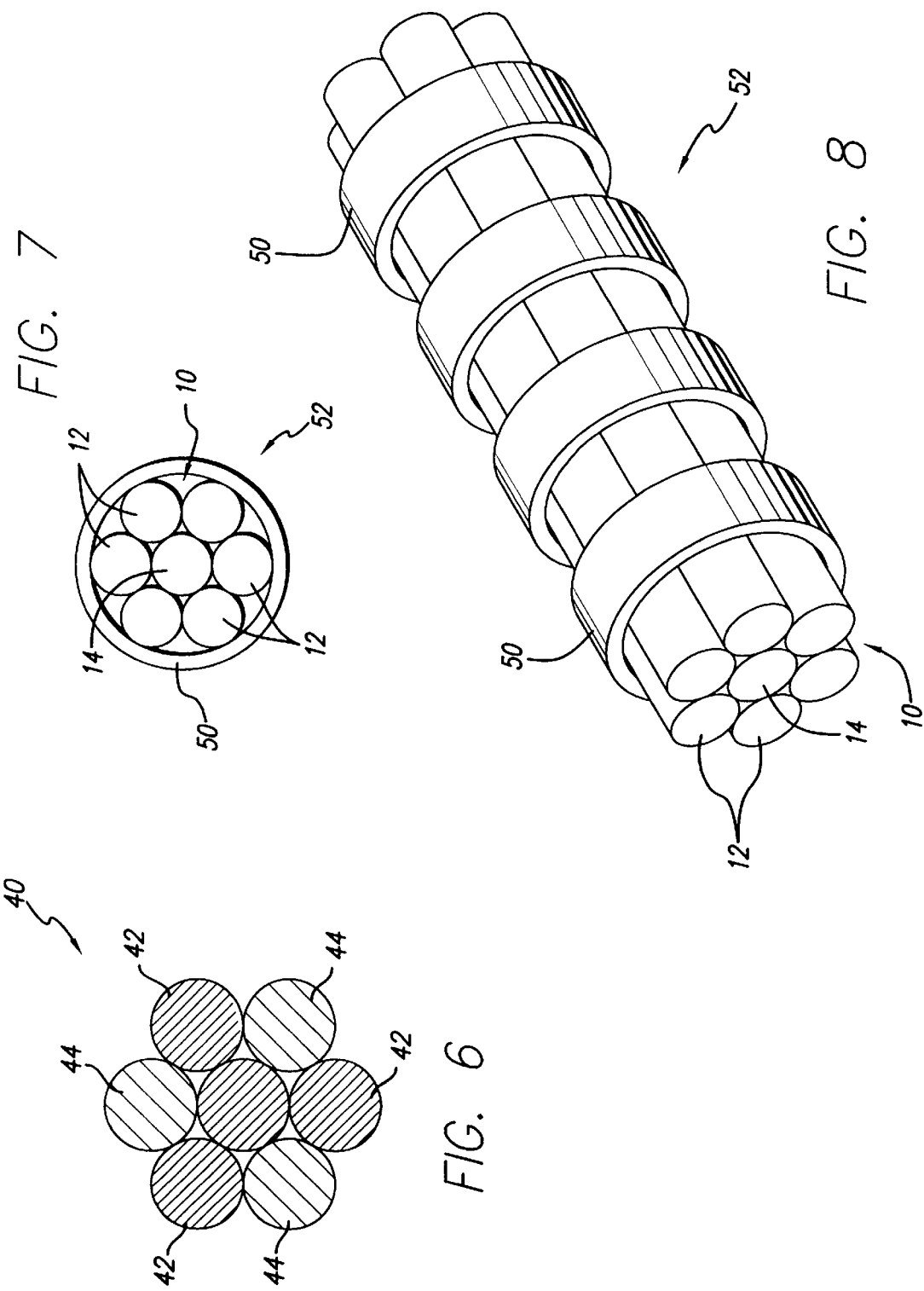

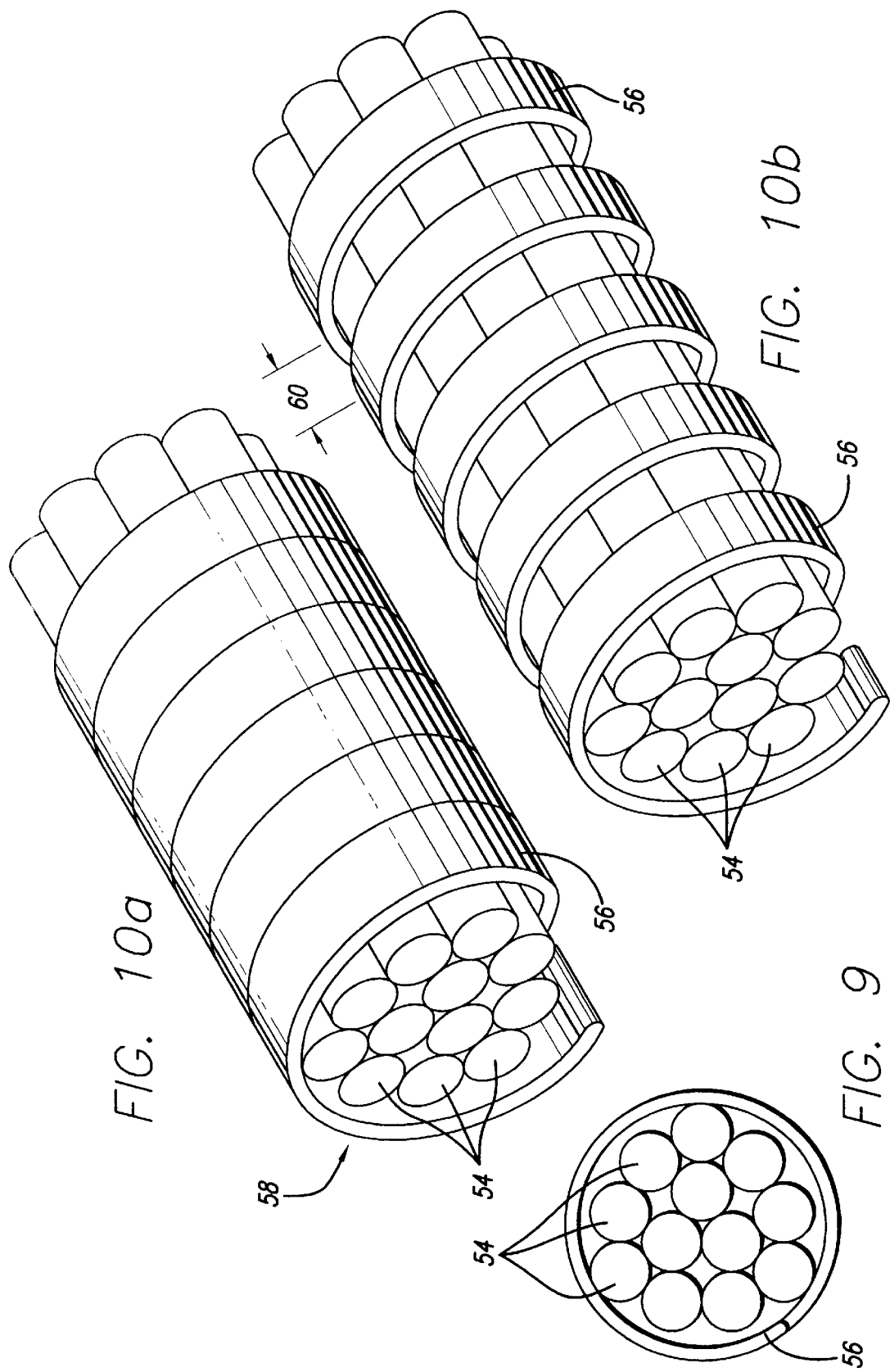

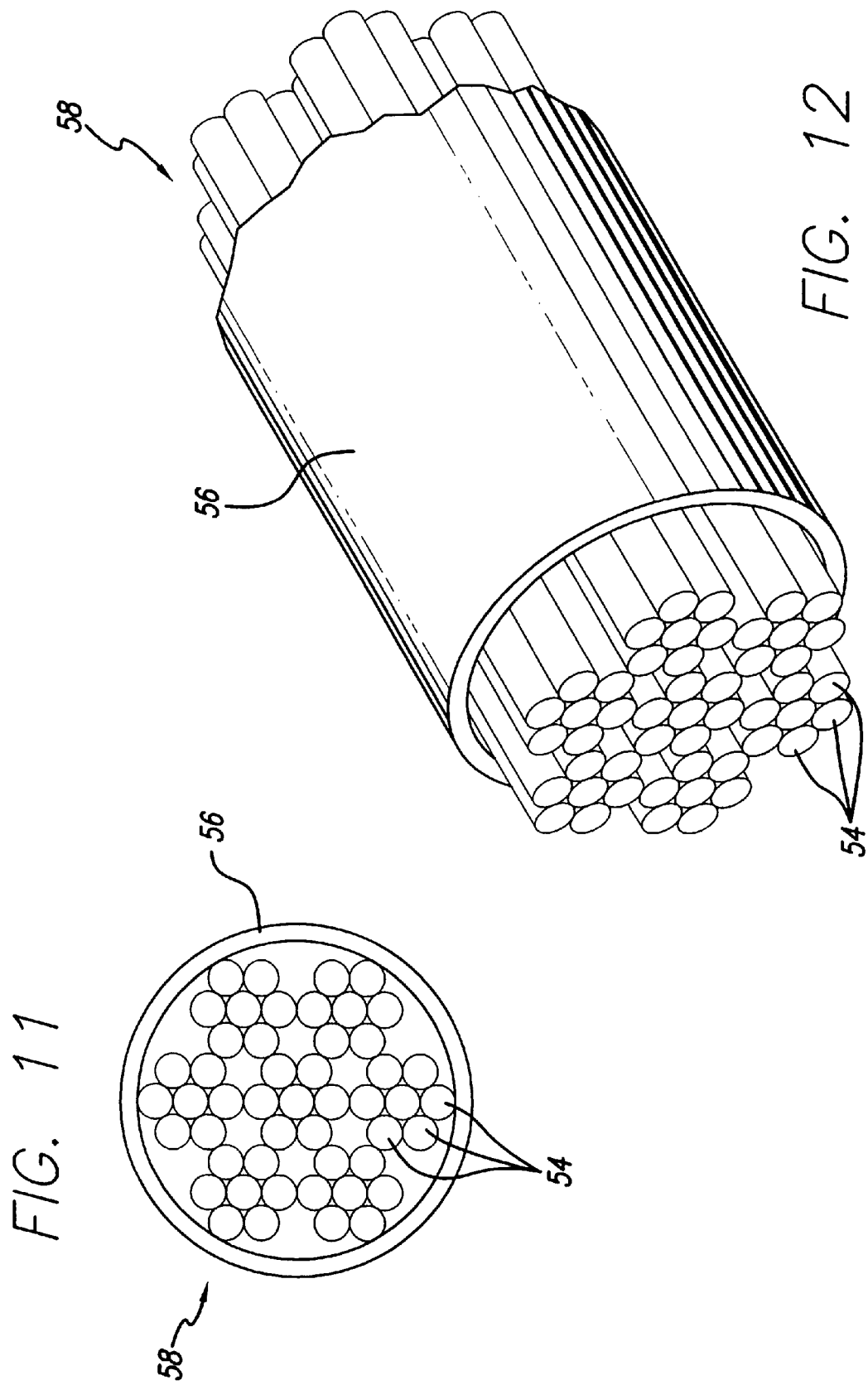

THREE DIMENSIONAL, LOW FRICTION VASOOCCLUSIVE COIL, AND METHOD OF MANUFACTURE

BACKGROUND OF THE INVENTION

1. Field of the Invention

This invention relates generally to vasoocclusive devices, and more particularly concerns a vasoocclusive device that has a first elongated, reduced friction configuration in which the vasoocclusive device may be deployed through a catheter or cannula to an anatomical cavity at a site in the vasculature to be treated, and that has a three dimensional second configuration assumed by the vasoocclusive device at the site to be treated for filling the anatomical cavity.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate, which can potentially be released during vascular surgery.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed.

One conventional vasoocclusive coil is known, for example, that has a three dimensional in-filling coil configuration, formed by winding a wire into a helix, and then winding the helix into a secondary form which forms a generally spherical shape, by winding the primary coil about poles placed on winding mandrel. The secondary wound coil is then annealed on the winding mandrel, and the coil is then removed from the winding mandrel and loaded into a carrier for introduction into a delivery catheter. Another similar type of vasoocclusive device is known that can be formed from one or more strands, and can be wound to form a generally spherical or ovoid shape when released and relaxed at the site to be treated. Another implantable vasoocclusive device having multiple secondary layers of primary windings has a final shape that is a generally spherical coil formed of linear or helical primary coils that are wound into a secondary form having three layers. The inner winding is wound and then the second layer formed by winding in the opposite direction of the first layer. The final configuration is a chunky or stepped shape approximately a sphere, ovoid, or egg. Yet another conventional implant for vessel occlusion is made from helical elements of metal or synthetic material by twisting or coiling the elements and forming them into a secondary shape such as a rosette or double rosette for implantation using a catheter, and another vasoocclusive device is known that has a final conical shape. However, due to the tendency of such three dimensional shaped coils to transform into their expanded, final forms when introduced into a catheter in the body, they are inherently more difficult than a helical coil or a straight wire or micro-cable to push through such a catheter for delivery to a site in the vasculature to be treated, due to friction between the coil and the catheter through which it is delivered to the site to be treated, which can even result in misalignment of the coil within the catheter during delivery.

There thus remains a need for a vasoocclusive device that has a three dimensional final form that can be used to fill an anatomical cavity at a site in the vasculature to be treated, reduces friction between the coil and the catheter through which it is delivered to the site to be treated, and ultimately helps to prevent coil misalignment. The present invention meets these and other needs.

SUMMARY OF THE INVENTION

Briefly, and in general terms, the present invention provides for an improved vasoocclusive coil, and a method of making the coil, that has a distal portion that is three dimensionally shaped, and a proximal portion that is linear or helically shaped, in order to combine the best qualities of a three dimensional coil and a linear or helical coil. The distal three dimensional portion will form a basket for filling the anatomical cavity at the site in the vasculature to be treated, while the proximal portion will fill and reinforce the basket. This combination will reduce friction within a catheter or cannula being used to deliver the vasoocclusive coil to the site in the vasculature to be treated, and ultimately helps prevent coil realignment or misalignment. The ultimate coil volume that otherwise might be limited due to frictional constraints of three dimensional coils will not be compromised with the device of the present invention.

The present invention accordingly provides for a vasoocclusive device that is adapted to be inserted into a portion of a vasculature for occluding the portion of the vasculature for use in interventional therapy and vascular surgery. The vasoocclusive device comprises at least one strand of a flexible material formed to have an a first inoperable, substantially linear configuration for insertion into and through a catheter or cannula to a desired portion of the vasculature to be treated, and a second operable, three dimensional configuration for occluding the desired portion of the vasculature to be treated. The vasoocclusive device advantageously has a distal portion having a second operable, three dimensional shape for filling the anatomical cavity at the site in the vasculature to be treated, and a proximal portion having a second operable, substantially linear shape for filling and reinforcing the distal, three dimensional shaped portion when it is implanted at the site in the vasculature to be treated.

The present invention also provides for a method of making the vasoocclusive device. The method generally comprises the steps of winding at least one strand of a flexible shape memory material about a mandrel formed of a refractory material in a three dimensional configuration of the vasoocclusive coil to form a distal portion of the vasoocclusive coil; heating the at least one strand of a flexible shape memory material wound about the mandrel for a sufficient period of time to impart the form to the shape memory material included in the device to form an operable, three dimensional configuration of the vasoocclusive coil; removing the vasoocclusive coil from the mandrel; and cold working the vasoocclusive coil into a desired elongated configuration for placement into a catheter or cannula for use. In one presently preferred embodiment, the mandrel about which the at least one flexible strand forming the vasoocclusive coil is wound has a substantially spherical body portion having a plurality of circumferential grooves to form a three dimensional configuration of a distal portion of the vasoocclusive coil. In another presently preferred embodiment, the mandrel about which the at least one flexible strand forming the vasoocclusive coil is wound has a substantially spherical body with a plurality of posts disposed on the body. In a preferred aspect, six posts are disposed on the body aligned with the three orthogonal x, y and z axes through the body of the mandrel, for aligning and shaping the distal portion of the vasoocclusive device as it is wound on the mandrel. One of the posts is preferably made longer than the other posts, to serve as a mandrel for helically winding the proximal portion of the vasoocclusive coil. In another preferred aspect of the method, the step of heating comprises heating the at least one strand of a flexible shape memory material wound about the mandrel at a temperature of about 1100° F. for at least about 4 hours to impart the form to the shape memory material included in the device to form an operable, three dimensional configuration of the distal portion of the vasoocclusive coil.

These and other aspects and advantages of the invention will become apparent from the following detailed description and the accompanying drawings, which illustrate by way of example the features of the invention.

BRIEF DESCRIPTION OF THE DRAWINGS

FIG. 6 is an alternate preferred embodiment of the invention including a plurality of radiopaque strands within the cable.

FIG. 7 is an alternate preferred embodiment of the present invention wherein strands of the cable are arranged within an exterior binding consisting of multiple straps about the cable.

FIG. 8 is a perspective view of the embodiment of FIG. 7.

FIG. 9 is an alternative embodiment to the embodiment of FIG. 8 wherein the external binding of the cable represents a sheath wound about the cable.

FIGS. 10a and 10b are perspectives of alternative embodiments of the embodiment of FIG. 9.

FIG. 11 is a cross-section of an alternative embodiment in which a plurality of multi-strand cables are included within an external sheath surrounding the cable.

FIG. 12 is a perspective view of the embodiment of FIG. 11.

DETAILED DESCRIPTION OF THE PREFERRED EMBODIMENTS

Figure 1:
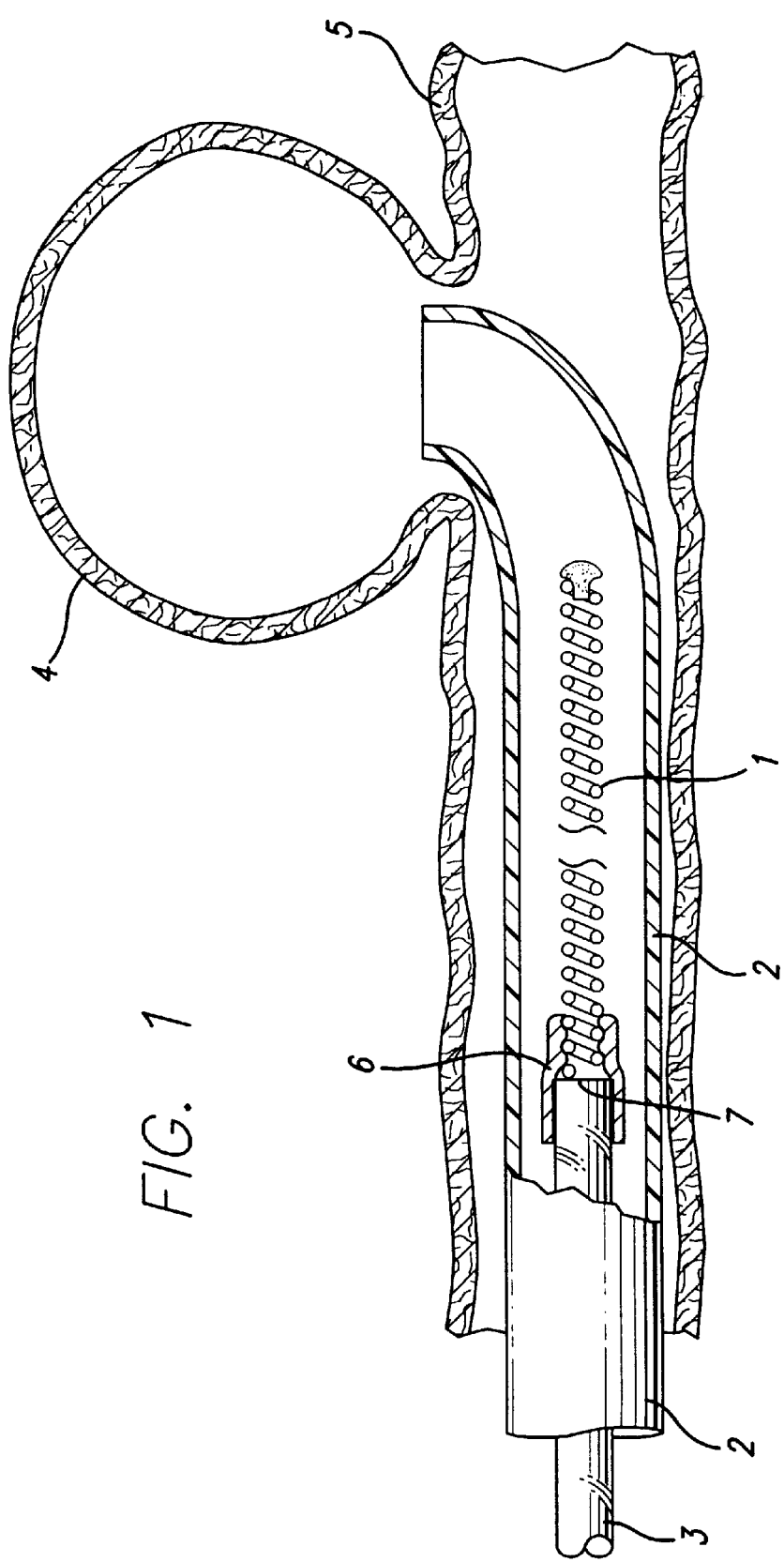
FIG. 1 is a cross section of a vascular member with an aneurysm illustrating the approach of a vasoocclusive coil towards the aneurysm.

While conventional three dimensional and spherical vasoocclusive coils have been developed, such three dimensional shaped coils tend to transform into their expanded, final forms when introduced into a catheter in the body, making them inherently more difficult than a simple helical coil or straight wire to push through a catheter or cannula for delivery to a site in the vasculature to be treated, due to friction between the coil and the catheter through which it is delivered to the site to be treated, and that can even result in misalignment of the coil within the catheter during delivery.

As is illustrated in the drawings, the invention is accordingly embodied in a vasoocclusive device that is adapted to be inserted into a portion of a vasculature for occluding the portion of the vasculature for use in interventional therapy and vascular surgery. The vasoocclusive coil 1 is formed from at least one strand of a flexible material formed to have a first inoperable, substantially linear configuration, as illustrated in FIG. 1, for insertion through a micro-catheter 2 into a desired portion of the vasculature to be treated, such as an aneurysm, or other anatomical malformation of the vasculature to be treated, and a second operable, three dimensional configuration, as illustrated in FIGS. 2 and 3, for occluding the desired portion of the vasculature to be treated.

FIG. 1 illustrates a helically wound vasoocclusive coil 1 which is formed to fit within the micro-catheter for insertion into an area upon which a therapeutic procedure is to be performed. FIG. 1 further shows a catheter pusher member 3 for delivering a vasoocclusive coil 1 for insertion into an aneurysm 4 projecting laterally from a blood vessel 5. The end of the micro-catheter 2 is typically introduced into the opening of the aneurism by use of a guide wire (note shown), and the coil and pusher member are introduced into the micro-catheter to insert the vasoocclusive coil into the aneurysm. In a presently preferred embodiment, catheter pusher member to which the vasoocclusive coil is mounted is an optical fiber pusher which is attached to the coil by a collar 6 of shape memory material as described in co-pending application Ser. Nos. 09/019,814 and 09/072,314 the disclosure of which are incorporated herein by reference. The vasoocclusive coil is typically introduced into the aneurysm and is then pushed from the micro-catheter until the vasoocclusive coil fills the cavity.

In one presently preferred embodiment, the shape memory collar 6 is heated to a temperature which allows it to be shrunk onto the vasoocclusive coil. The collar can be attached to optical fiber pusher by an adhesive which retains high strength at temperatures beyond the shape memory material transition point. After insertion, and when an operator is satisfied that the device is properly deployed, light energy from a source of coherent light is introduced into the proximal end of the optical fiber (not shown) and propagated in the distal end 7 of the fiber to cause the shape memory material collar to return to its previous shape and release the vasoocclusive coil. Those skilled in the art will recognize that the invention can also be used with a variety of other placement catheter systems, and it is not intended that the invention be limited to the placement concepts illustrated by way of example.

Figure 2:
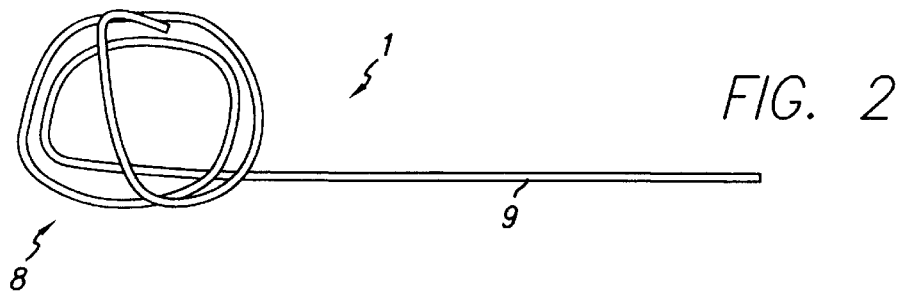
FIG. 2 is a side elevational view showing a first embodiment of a second operable, three dimensional configuration of the vasoocclusive coil of the invention.
Figure 3:
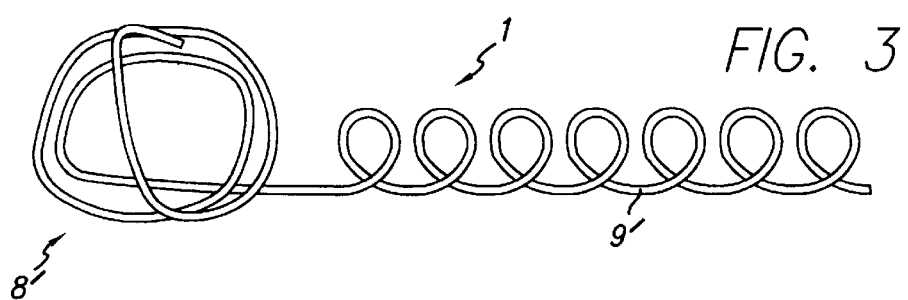
FIG. 3 is a side elevational view showing a second embodiment of a second operable, three dimensional configuration of the vasoocclusive coil of the invention.

Referring to FIGS. 2 and 3, the vasoocclusive device preferably has a distal portion 8 having a second operable, three dimensional shape for filling the anatomical cavity at the site in the vasculature to be treated, and a proximal portion having a second operable, substantially linear shape for filling and reinforcing the distal, three dimensional shaped portion when the vasoocclusive device is implanted at the site in the vasculature to be treated. The distal portion preferably has a second operable, three dimensional shape that is substantially spherical. As is illustrated in FIG. 2, in one presently preferred embodiment, the proximal portion 9 is substantially linear, and as is illustrated in FIG. 3, in another presently preferred embodiment, the proximal portion 9' is substantially helical.

Figure 4:
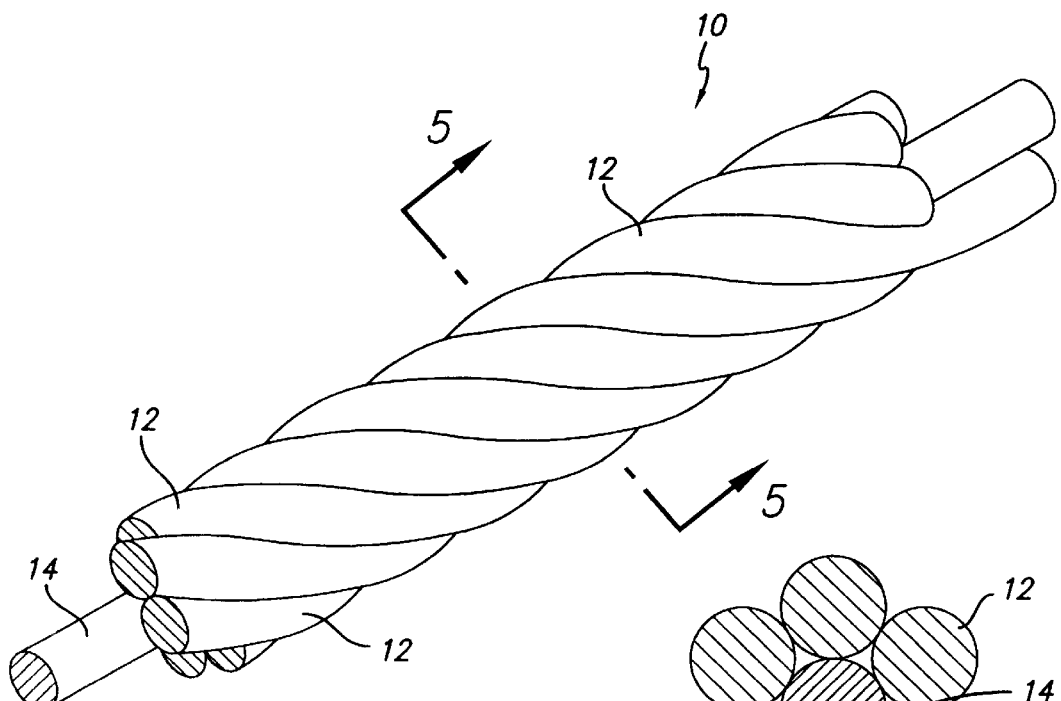
FIG. 4 is a perspective view of a radiopaque microstrand cable used in forming the vasoocclusive coil according to the invention.

In a presently preferred aspect of the invention, the vasoocclusive coils are formed from a multi-stranded micro-cable, although the vasoocclusive coils can also be made from a single strand of a flexible material formed to have an a first inoperable, substantially linear configuration for insertion into and through a catheter or cannula to a desired portion of the vasculature to be treated, and a second operable, three dimensional configuration for occluding the desired portion of the vasculature to be treated. As is illustrated in FIG. 4, the vasoocclusive coils are preferably formed from a multi-stranded micro-cable 10 that is typically approximately from 0.0021 to 0.0045 inches in diameter, and comprises a plurality of flexible strands 12 of nickel-titanium alloy, with at least one centrally, axially disposed radiopaque wire 14 which is approximately from 0.0007 to 0.0015 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker of the deployed configuration of a device made of the cable during vascular surgery.

There are numerous benefits to the novel construction of the invention for use in interventional devices and the like. By using the stranded or micro-cable construction of the invention, a vasoocclusive device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions.

Figure 5:
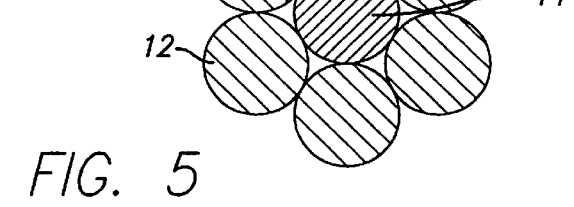
FIG. 5 is a cross-section at 5—5 of FIG. 4.

FIG. 5 is a cross-section of the micro-cable of FIG. 4 at 5—5 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter or cannula. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 5, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

While one presently preferred implementation of the micro-cable of the invention has been illustrated, those skilled in the art will appreciate that other variations of the invention may have advantages for certain purposes. FIG. 6 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

FIG. 7 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 8 is a perspective view of the banded cable 50 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. As a further alternative embodiment, it is possible for the longitudinal cable 52 to be formed of a single inner cable 10 with bands 50.

FIG. 9 illustrates a further embodiment of the invention in which longitudinal strands of cables are contained within a wound cover 56 for the purposes of providing a composite guide wire or the like 58 having improved torqueability. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 10a and 10b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

FIGS. 11 and 12 illustrate a cross-section of a micro-cable according to the invention which has at least one overall exterior sheath to contain the microcable. The micro-cable may be made of one or more multiple strand elements which may further include twisted or longitudinal strands within their construction. The sheath may also be used to control the torqueability characteristics of the cable and as discussed in co-pending application, Ser. No. 08/986,004, the sheath may be multi-layered with different materials in order to provide a graduated bending and stiffness characteristic over the length of the cable.

It will be appreciated that a three dimensional occlusive device adapted to be inserted into a portion of a vasculature for occluding the portion of the vasculature for use in interventional therapy and vascular surgery, can be formed as described above, from at least one multi-stranded micro-cable having a plurality of flexible strands of a resilient material, with at least one radiopaque strand to provide a radiopaque marker for the device during vascular surgery. The occlusive device is configured to have a first inoperable, substantially linear, elongated configuration for insertion into and through a catheter or cannula to a desired portion of the vasculature to be treated, and a second operable, three dimensional configuration for occluding the desired portion of the vasculature to be treated.

In the method of making the vasoocclusive coils of the invention, a mandrel is used for annealing the coils in the desired second operable, three dimensional shape. A mandrel suitable for making such second operable, three dimensional shaped occlusive devices can be formed of a refractory material, such as alumina or zirconia, for example. The mandrel typically has the general three dimensional shape that the occlusive device will be given, and can have a generally helical, conical, or spherical shape, or can have a unique shape designed to provide such a primary configuration to the occlusive device. The mandrel forms a support for the winding and heat treatment of the micro-cable, plurality of microcables, or composite micro-cable occlusive device as described above, and ideally will not contaminate the occlusive device during heat treatment of the device.

Figure 13A:
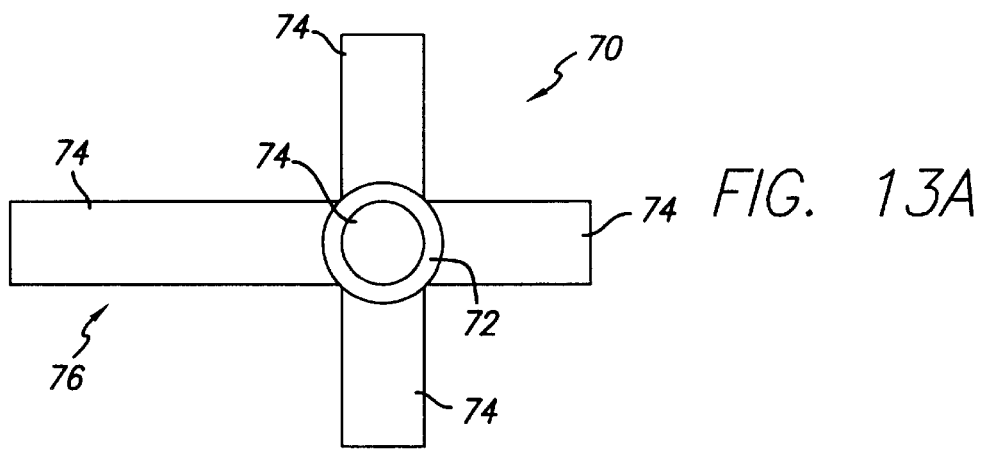
FIG. 13A is a top plan view of a first embodiment of a mandrel used for making the vasoocclusive coil according to the method of the invention.
Figure 14:
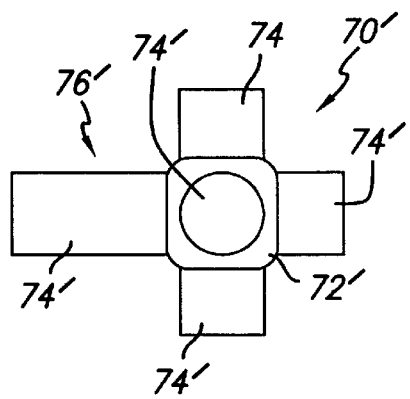
FIG. 14 is a plan view of a variant of the first embodiment of FIGS. 13A and 13B.
Figure 13B:
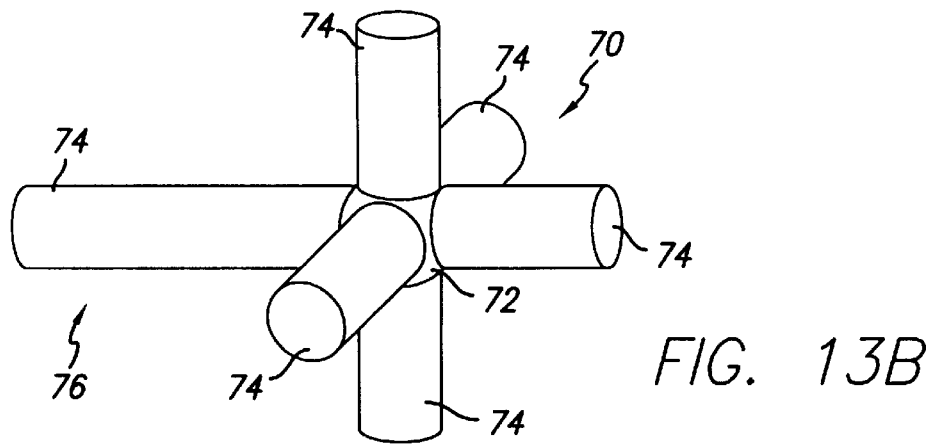
FIG. 13B is a perspective view of the mandrel of FIG. 13A.
Figure 15C:
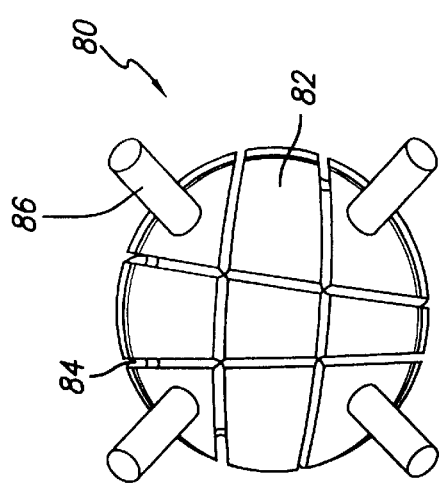
FIG. 15C is a bottom plan view of the mandrel of FIG. 15A.
Figure 15F:
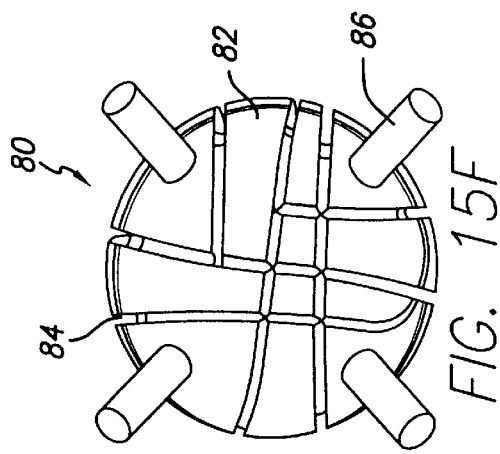
FIG. 15F is a rear plan view of the mandrel of FIG. 15A.
Figure 15B:
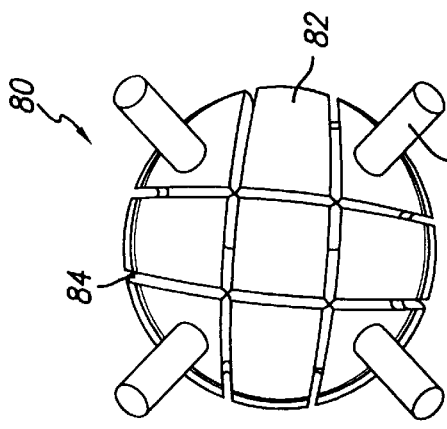
FIG. 15B is a front plan view of the mandrel of FIG. 15A.
Figure 15E:
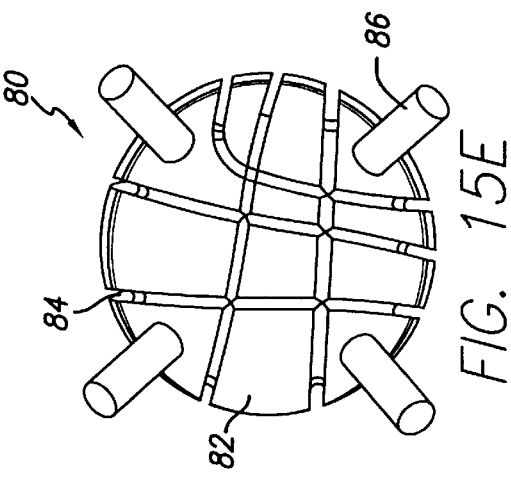
FIG. 15E is a right side plan view of the mandrel of FIG. 15A.
Figure 15A:
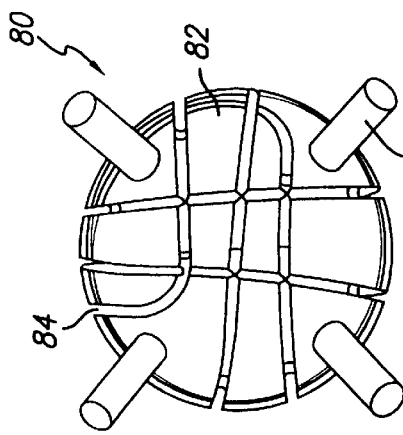
FIG. 15A is a top plan view of a second preferred embodiment of a mandrel used for making the vasoocclusive coil according to the method of the invention.
Figure 15D:
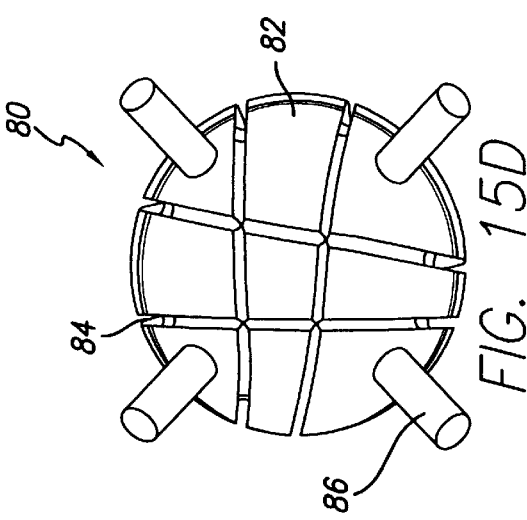
FIG. 15D is a left side plan view of the mandrel of FIG. 15A.
Figure 16B:
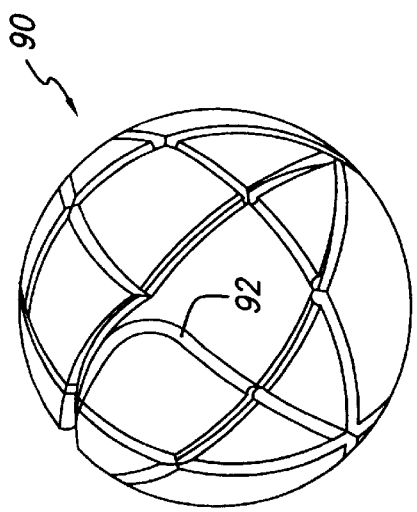
FIG. 16B is a bottom plan view of the mandrel of FIG. 16A.
Figure 16E:
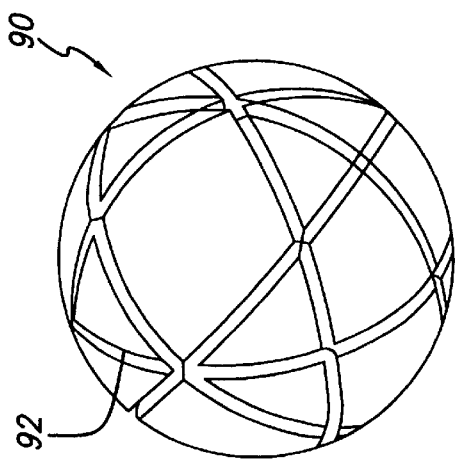
FIG. 16E is a rear plan view of the mandrel of FIG. 16A.
Figure 16C:
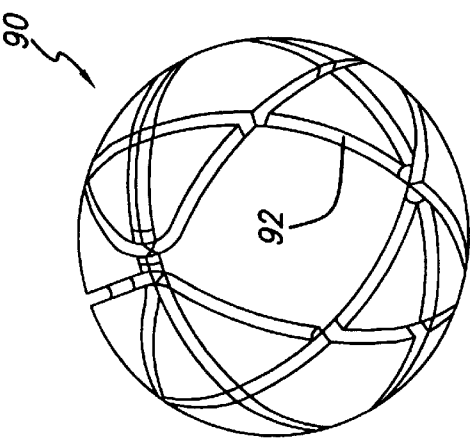
FIG. 16C is a left side plan view of the mandrel of FIG. 16A.
Figure 16A:
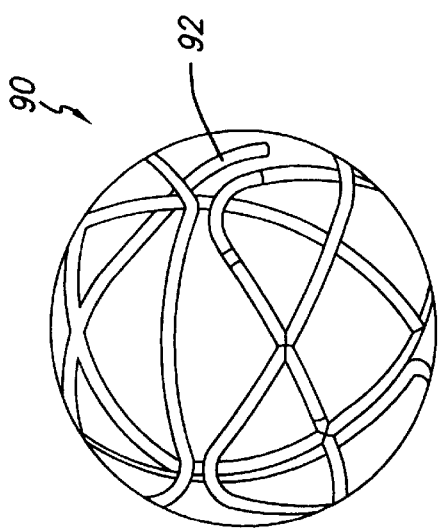
FIG. 16A is a front plan view of a third preferred embodiment of a mandrel used for making the vasoocclusive coil according to the method of the invention.
Figure 16D:
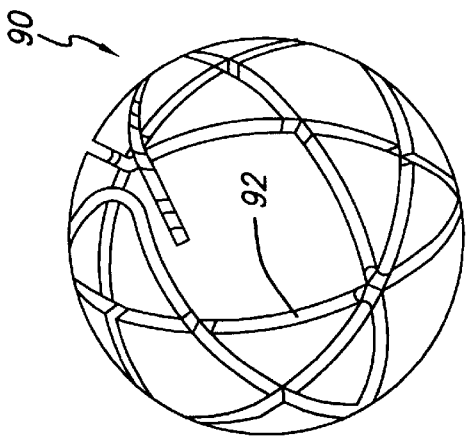
FIG. 16D is a right side plan view of the mandrel of FIG. 16A.
Figure 17A:
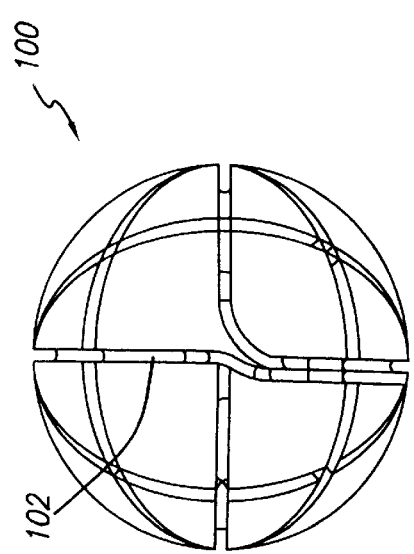
FIG. 17A is a top plan view of a fourth preferred embodiment of a mandrel used for making the vasoocclusive coil according to the method of the invention.
Figure 17B:
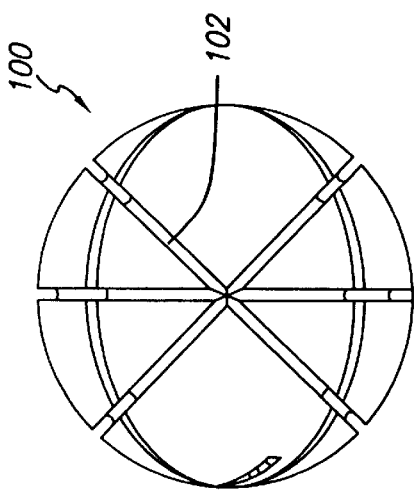
FIG. 17B is a front plan view of the mandrel of FIG. 17A.
Figure 17E:
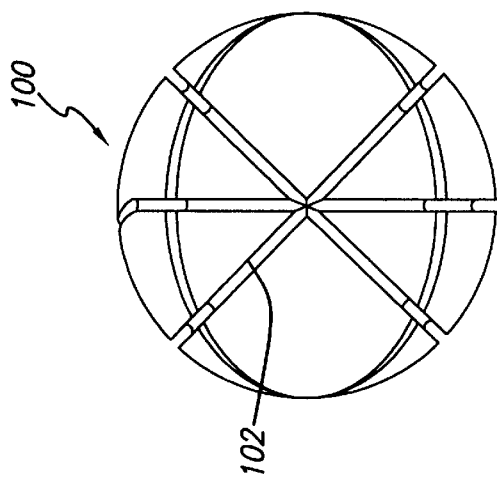
FIG. 17E is a right side plan view of the mandrel of FIG. 17A.
Figure 17C:
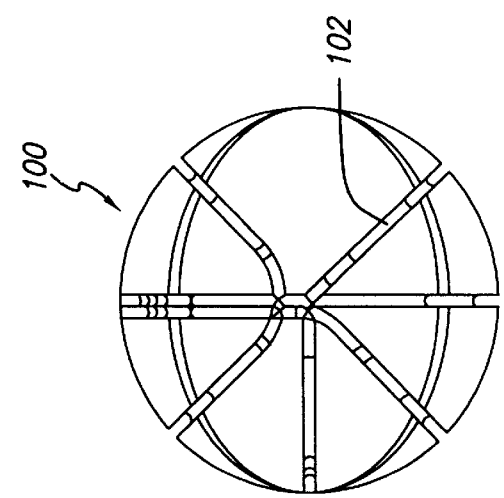
FIG. 17C is a bottom plan view of the mandrel of FIG. 17A.
Figure 17D:
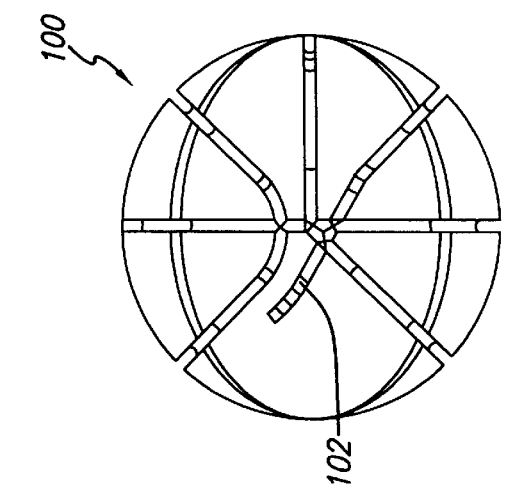
FIG. 17D is a left side plan view of the mandrel of FIG. 17A.

In one presently preferred embodiment illustrated in FIGS. 13A and 13B, one or more of the flexible strands forming the vasoocclusive coil are wound around the surface of a mandrel 70 having a substantially spherical main body 72 with six cylindrical posts 74 having a diameter slightly smaller than that of the main body, disposed on the body and aligned with the three orthogonal x, y and z axes through the body of the mandrel, for aligning and shaping the distal portion of the vasoocclusive device as it is wound on the mandrel. Preferably one of the posts 76 is longer than the other posts, to serve as a mandrel for helically winding the proximal portion of the vasoocclusive coil. As is shown in FIG. 14, in a presently preferred variant of the embodiment of FIGS. 13A and 13B, the mandrel 70' has a main body 72' that is substantially cubical, with the six cylindrical posts 74' disposed on each of the faces of the main body, and one of the posts 76' being longer than the others.

In another presently preferred embodiment illustrated in FIGS. 15A to 15F, one or more of the flexible strands forming the vasoocclusive coil are wound around the surface of a mandrel 80 having a substantially spherical main body 82, with a plurality of circumferential grooves 84 defined on the surface of the main body, and a plurality of posts 86 mounted on the main body of the mandrel for aligning the occlusive device as it is wound on the mandrel.

In another presently preferred embodiment illustrated in FIGS. 16A to 16E, one or more of the flexible strands forming the vasoocclusive coil are wound around the surface of a substantially spherical mandrel 90 having a plurality of circumferential grooves 92 for aligning the occlusive device as it is wound on the mandrel.

FIGS. 17A to 17E illustrate another presently preferred embodiment of a substantially spherical mandrel 100 having a plurality of circumferential grooves 102 for aligning the occlusive device, in which one or more of the flexible strands forming the vasoocclusive coil are wound around the surface of the mandrel.

The surface of the mandrel may also have one or more apertures for receiving one or more ends of the strands, to assist winding into the desired form. The wound occlusive device is preferably heat treated at a suitable temperature and a sufficient period of time to impart the form to the shape memory material included in the device. While heat treatment at a temperature of about 1100° F. for approximately 4 hours or more is typically sufficient to impart the form to the occlusive device when the shape memory material is a nickel titanium super-elastic alloy, although the temperature utilized can be substantially lowered, and the duration of heat treatment adjusted accordingly, as will be appreciated by those skilled in the art. After the heat treatment, the occlusive device is removed from the mandrel, and cold worked into the desired collapsed elongated configuration for placement into a catheter or cannula for use. When the occlusive device reaches its destination in the vasculature during vascular therapy, it assumes the primary shape imparted from the heat treatment on the mandrel.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A vasoocclusive device that is adapted to be inserted into a portion of a vasculature for occluding the portion of the vasculature for use in interventional therapy and vascular surgery, comprising:

at least one multi-stranded micro-cable formed to have a first inoperable, substantially linear configuration for insertion into and through a catheter to a desired portion of the vasculature to be treated, and a second operable, three dimensional configuration for occluding the desired part of the vasculature to be treated; said vasoocclusive device further having a distal portion having a second operable, three dimensional shape for filling the anatomical cavity at the site in the vasculature to be treated, and a proximal portion having a second operable, substantially linear shape for filling and reinforcing the distal, three dimensional shaped portion when the vasoocclusive device is implanted at the site in the vasculature to be treated, each said multi-stranded micro-cable having a plurality of flexible strands of a resilient material comprising a central core, and at least one radiopaque strand to provide a radiopaque marker of the deployed configuration of a device made of the cable during vascular surgery.

2. The vasoocclusive device of claim 1, wherein said distal portion has a second operable, three dimensional shape that is substantially spherical.

3. The vasoocclusive device of claim 1, wherein said proximal portion is substantially linear.

4. The vasoocclusive device of claim 1, wherein said proximal portion is substantially helical.

5. The vasoocclusive device of claim 1, wherein said plurality of strands are helically wound.

6. The vasoocclusive device of claim 1, wherein said plurality of flexible strands are parallel longitudinal strands.

7. The vasoocclusive device of claim 1, wherein at least one of said plurality of strands comprises a super-elastic material.

8. The vasoocclusive device of claim 1, wherein said plurality of flexible strands of a resilient material are comprised of a shape memory material.

9. The vasoocclusive device of claim 8, wherein said shape memory material comprises a nickel-titanium alloy.

10. The vasoocclusive device of claim 9, wherein said shape memory nickel-titanium alloy is heat treated such that the alloy is highly flexible at a temperature appropriate for introduction into the body via a catheter, and after placement, the device will take on the primary coil configuration.

11. The vasoocclusive device of claim 8, wherein said shape memory material comprises a shape memory polymer.

12. The vasoocclusive device of claim 1, wherein said plurality of strands comprises a plurality of exterior strands surrounding at least one interior strand.

13. The vasoocclusive device of claim 1, wherein said plurality of strands comprises a plurality of exterior strands surrounding said central core.

14. The vasoocclusive device of claim 1, wherein said radiopaque strand comprises at least one centrally, axially disposed radiopaque wire.

15. The vasoocclusive device of claim 1, wherein said radiopaque wire is made of platinum.

16. The vasoocclusive device of claim 1, wherein said radiopaque wire is made of tungsten.

17. The vasoocclusive device of claim 1, wherein said radiopaque wire is made of gold.

18. The vasoocclusive device of claim 1, wherein said plurality of strands comprises a plurality of radiopaque strands.

19. The vasoocclusive device of claim 1, wherein said central core comprises copper.

20. The vasoocclusive device of claim 1, wherein said central core comprises a copper alloy.

21. The vasoocclusive device of claim 1, wherein said strands of the micro-cable are bundled by at least one outer cover to produce a composite banded cable.

22. A vasoocclusive device that is adapted to be inserted into a portion of a vasculature for occluding the portion of the vasculature for use in interventional therapy and vascular surgery, comprising:
   at least one multi-stranded micro-cable formed to have a first inoperable, substantially linear configuration for insertion into and through a catheter to a desired portion of the vasculature to be treated, and a second operable, three dimensional configuration for occluding the desired part of the vasculature to be treated; said vasoocclusive device further having a distal portion having a second operable, three dimensional shape for filling the anatomical cavity at the site in the vasculature to be treated, and a proximal portion having a second operable, substantially linear shape for filling and reinforcing the distal, three dimensional shaped portion when the vasoocclusive device is implanted at the site in the vasculature to be treated, each said multi-stranded micro-cable having a plurality of flexible strands of a resilient material comprising a central core, and at least one radiopaque strand to provide a radiopaque marker of the deployed configuration of a device made of the cable during vascular surgery, and wherein said strands of the micro-cable are bundled by a least one outer cover comprising a sheath to constrain said strands about a longitudinal axis to produce a composite banded cable.

23. The vasoocclusive device of claim 22, wherein said outer cover comprises an outer sheath of material to provide bending stiffness and constrain said strands about said longitudinal axis.

24. The vasoocclusive device of claim 23, wherein said sheath comprises a containment strand wound about said longitudinal strands.

25. The vasoocclusive device of claim 23, wherein said sheath is made of low friction material.

26. The vasoocclusive device of claim 23, wherein said sheath is made of a fluoropolymer.

27. The vasoocclusive device of claim 23, wherein said sheath comprises a heat shrinkable plastic tube.

28. The vasoocclusive device of claim 21, wherein said strands are bundled by a plurality of bands disposed at intervals to produce a composite banded cable.

29. The vasoocclusive device of claim 28, wherein said strands are laid parallel within the composite banded cable.

30. The vasoocclusive device of claim 28, wherein said strands are twisted within the composite banded cable.

31. The vasoocclusive device of claim 28, wherein composite cable comprises a single inner micro-cable.

32. The vasoocclusive device of claim 28, wherein said exterior wrapped cover is wound at varying intervals along the outside to provide variations in the torqueability and stiffness of the composite cable.

33. The vasoocclusive device of claim 32, wherein the width of the outer cover is varied along the composite cable.

34. The vasoocclusive device of claim 28, wherein said outer covering varies in cross section along its length to provide bending stiffness of said composite cable which varies along said composite cable.

35. The vasoocclusive device of claim 21, wherein the number of strands and the degree to which they extend along said composite cable within the outer covering varies along said composite cable.

36. The vasoocclusive device of claim 23, wherein outer covering comprises a plurality of layers formed of different materials in order to provide a graduated bending and stiffness characteristic.

37. The vasoocclusive device of claim 28, wherein said composite microcable comprises a plurality of micro-cables disposed within said outer cover in order to provide desired bending and strength characteristics.

38. The vasoocclusive device of claim 35, wherein said plurality of micro-cables are helically wound within said outer cover.

39. The vasoocclusive device of claim 35, wherein said plurality of micro-cables extend parallel and longitudinally within said outer cover.

40. The vasoocclusive device of claim 35, wherein said plurality of micro-cables are bundled by at least one outer cover to produce said composite banded cable.

41. The vasoocclusive device of claim 40, wherein said plurality of micro-cables are banded at intervals by a plurality of bands.

42. A method of making a vasoocclusive device that is adapted to be inserted into a portion of a vasculature for occluding the portion of the vasculature for use in interventional therapy and vascular surgery, said vasoocclusive device being formed from at least one strand of a flexible shape memory material formed to have a first inoperable, substantially linear configuration for insertion into and through a catheter to a desired portion of the vasculature to be treated, and a second operable, three dimensional configuration for occluding the desired portion of the vasculature to be treated, said vasoocclusive device having a distal portion having a second operable, three dimensionally shape, and a proximal portion having a second operable, substantially linear shape, the method comprising the steps of:
   winding at least one strand of a flexible shape memory material about a mandrel in a three dimensional configuration of the vasoocclusive coil to form a distal portion of the vasoocclusive coil;
   heating said at least one strand of a flexible shape memory material wound about the mandrel for a sufficient period of time to impart the form to the shape memory material included in the device to form an operable, three dimensional configuration of the vasoocclusive coil;
   removing the vasoocclusive coil from the mandrel; and
   cold working the vasoocclusive coil into a desired elongated configuration for placement into a catheter or cannula for use.

43. The method of claim 42, wherein the mandrel about which said at least one flexible strand forming the vasoocclusive coil is wound has a substantially spherical body portion having a plurality of circumferential grooves to form a three dimensional configuration of a distal portion of the vasoocclusive coil.

44. The method of claim 42, wherein the mandrel about which said at least one flexible strand forming the vasoocclusive coil is wound has a main body with a plurality of posts disposed on the body.

45. The method of claim 44, wherein six posts are disposed on the body aligned with the three orthogonal x, y and z axes through the body of the mandrel, for aligning and shaping the distal portion of the vasoocclusive device as it is wound on the mandrel.

46. The method of claim 44, wherein one of the posts is longer than the other posts, to serve as a mandrel for helically winding the proximal portion of the vasoocclusive coil.

47. The method of claim 44, wherein said main body is substantially spherical.

48. The method of claim 44, wherein said main body is substantially cubical.

49. The method of claim 42, wherein the step of heating comprises heating said at least one strand of a flexible shape memory material wound about a mandrel made of refractory material at a temperature of about 1100° F. for about at least 4 hours.

* * * * *

UNITED STATES PATENT AND TRADEMARK OFFICE
CERTIFICATE OF CORRECTION

PATENT NO. : 6,171,326 B1  Page 1 of 1
DATED : January 9, 2001
INVENTOR(S) : David A. Ferrera et al.

It is certified that error appears in the above-identified patent and that said Letters Patent is hereby corrected as shown below:

Column 12, claim 38,
Line 27, change "35", to read -- 37 --.

Column 12, claim 39,
Line 30, change "35", to read -- 37 --.

Column 12, claim 40,
Line 33, change "35", to read -- 37 --.

Signed and Sealed this

Thirteenth Day of November, 2001

Attest:

NICHOLAS P. GODICI
Attesting Officer  Acting Director of the United States Patent and Trademark Office